US011357932B2

United States Patent
Shlomovitz et al.

(10) Patent No.: US 11,357,932 B2
(45) Date of Patent: Jun. 14, 2022

(54) METHOD AND SYSTEM FOR DETECTING LEAKS AND/OR VERIFYING ADEQUATE CLOSURE FOLLOWING A MEDICAL PROCEDURE

(71) Applicant: QAELON MEDICAL, Strasbourg (FR)

(72) Inventors: Eran Shlomovitz, Ontario (CA); Lee L. Swanstrom, Portland, OR (US); Michele Diana, Lingosheim (FR)

(73) Assignee: QAELON MEDICAL, Strasbourg (FR)

( * ) Notice: Subject to any disclaimer, the term of this patent is extended or adjusted under 35 U.S.C. 154(b) by 758 days.

(21) Appl. No.: 14/668,380

(22) Filed: Mar. 25, 2015

(65) Prior Publication Data

US 2015/0272499 A1 Oct. 1, 2015

Related U.S. Application Data

(60) Provisional application No. 61/970,188, filed on Mar. 25, 2014.

(51) Int. Cl.
*A61M 13/00* (2006.01)
*A61B 1/015* (2006.01)
(Continued)

(52) U.S. Cl.
CPC .......... *A61M 13/003* (2013.01); *A61B 1/015* (2013.01); *A61B 5/036* (2013.01); *A61B 5/14503* (2013.01); *A61B 5/14507* (2013.01); *A61B 5/0002* (2013.01); *A61M 2016/1035* (2013.01); *A61M 2202/0225* (2013.01); *A61M 2202/0283* (2013.01); *A61M 2205/15* (2013.01); *A61M 2205/3334* (2013.01)

(58) Field of Classification Search
CPC ... A61B 5/4869; A61B 1/015; A61B 5/14507; A61B 5/14503; A61B 5/036; A61B 5/0002; A61M 13/003; A61M 2202/0283; A61M 2202/0225
See application file for complete search history.

(56) References Cited

U.S. PATENT DOCUMENTS

2005/0137529 A1* 6/2005 Mantell ............... A61M 13/003
604/129
2005/0222534 A1* 10/2005 Uesugi .................. A61B 50/10
604/26

(Continued)

FOREIGN PATENT DOCUMENTS

WO 2014/074105 A1 5/2014

*Primary Examiner* — Rene T Towa
(74) *Attorney, Agent, or Firm* — Maier & Maier, PLLC

(57) ABSTRACT

Method for detecting leaks and/or verifying adequate closure following a medical procedure, on a hollow or tubular organ of a subject, wherein a leak test is performed by injecting or insufflating, in the concerned organ, a specific test gas which is not commonly produced or naturally present within the body of the subject, or which is present or produced in a precisely known amount or concentration, and by analyzing percutaneously the gas or gas mixture present locally within the body cavity in which the organ is situated, and then verifying the presence, and preferably determining the concentration, of the injected or insufflated test gas in the local gas or gas mixture of the body cavity and indicating whether the concerned organ or a lumen defined by the latter is leak-free or not.

16 Claims, 9 Drawing Sheets

(51) Int. Cl.
*A61B 5/03* (2006.01)
*A61B 5/145* (2006.01)
*A61B 5/00* (2006.01)
*A61M 16/10* (2006.01)

(56) References Cited

U.S. PATENT DOCUMENTS

| | | | |
|---|---|---|---|
| 2005/0240093 A1* | 10/2005 | DeArmond | A61B 5/0538 600/372 |
| 2007/0000300 A1* | 1/2007 | Diemunsch | A61M 13/003 600/300 |
| 2007/0123781 A1 | 5/2007 | Callahan et al. | |
| 2007/0163604 A1* | 7/2007 | Mikkaichi | A61B 90/06 128/898 |
| 2007/0255165 A1* | 11/2007 | Uesugi | A61B 1/00135 600/560 |
| 2008/0033759 A1* | 2/2008 | Finlay | G16H 10/20 705/3 |
| 2013/0096399 A1* | 4/2013 | Scalici | B01D 39/00 600/309 |
| 2013/0289367 A1 | 10/2013 | Kruglick et al. | |
| 2014/0018696 A1 | 1/2014 | DeArmond | |
| 2014/0200437 A1* | 7/2014 | Yager | A61B 5/004 600/420 |
| 2014/0371550 A1* | 12/2014 | Hoffman | A61B 5/686 600/302 |

* cited by examiner

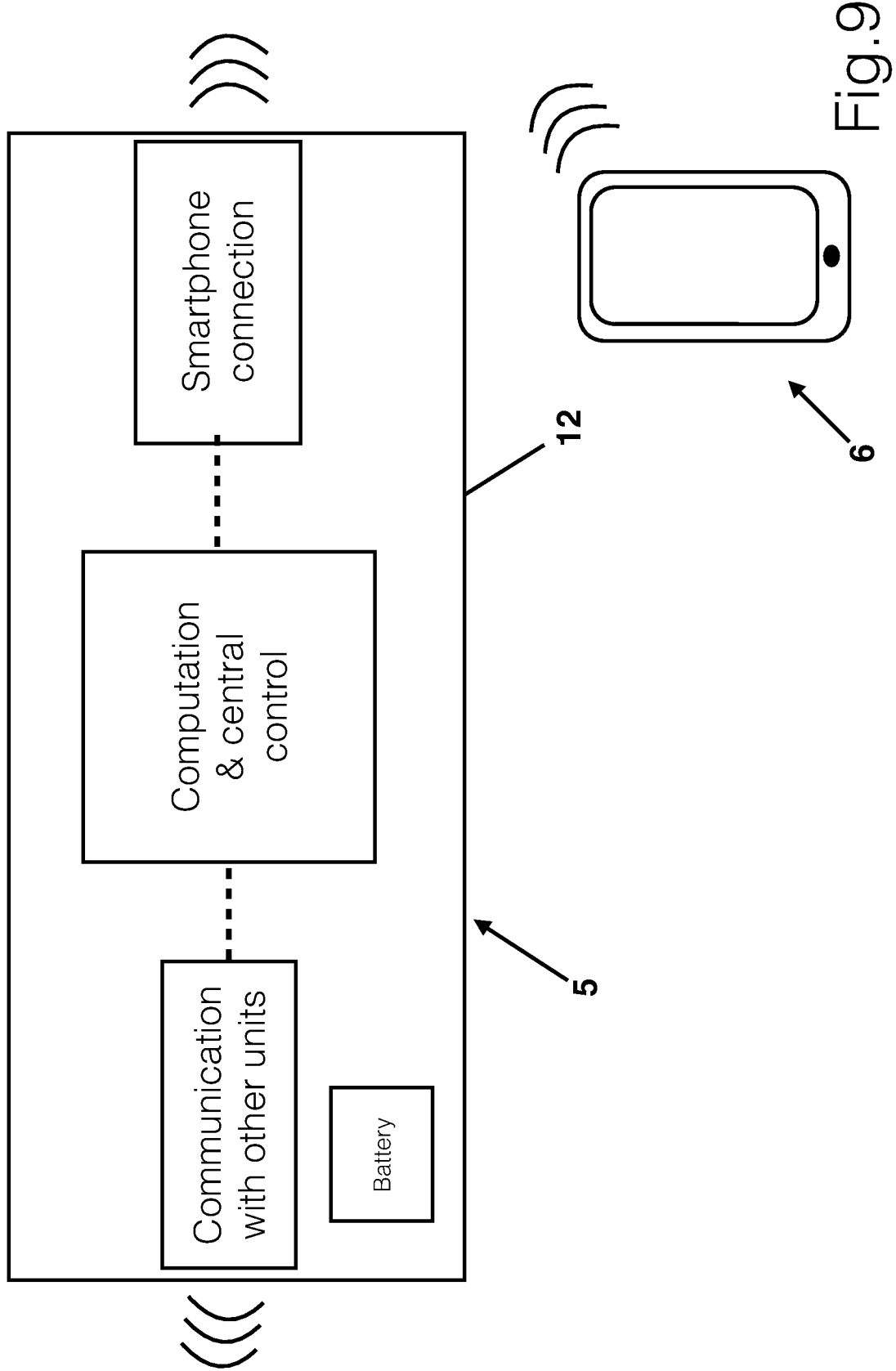

METHOD AND SYSTEM FOR DETECTING LEAKS AND/OR VERIFYING ADEQUATE CLOSURE FOLLOWING A MEDICAL PROCEDURE

FIELD OF THE INVENTION

The present invention concerns the field of medical procedures, methods, systems and devices, more specifically endoluminal related procedures and systems able to evaluate structural integrity and gas tightness of a lumen, or more generally of a hollow or tubular organ.

The invention is related more precisely to a method and a system for detecting leaks and/or verifying adequate closure following a medical procedure. Most preferably, the invention concerns a method and a system for detecting luminal leaks and/or verifying adequate luminal closure following an endoluminal procedure.

BACKGROUND OF THE INVENTION

When a medical procedure (mini-invasive or not) is performed on an organ which needs to show under normal circumstances of functioning a fluidic tightness towards its local environment, one must make sure that no discontinuity, nor any passage or opening is present in the organ wall(s) defining the concerned lumen or cavity.

Currently endoluminal therapeutic procedures are gaining in popularity and increasing in complexity. More specifically, therapeutic mini-invasive or endoscopy procedures span nowadays a broad range, from simple polypectomy, fistula, and leak repairs to more advanced procedures, including endoscopic submucosal dissections (ESD), creation of enteric anastamosis, Per Oral Endoscopic Myotomy (POEM), and full thickness resections. These procedures have the potential for tremendous patient and societal benefit, as they tend to be less morbid than other alternative treatments, enabling rapid return to normal activity.

Now, all endoluminal procedures, both diagnostic and therapeutic, are associated with a risk of perforation, at worst, a full thickness, intraperitoneal perforation. Whether created intentionally as part of a transluminal or extraluminal procedure, or as a result of unintentional complication, these perforations must be securely sealed to prevent post procedural morbidity. Fortunately, numerous endoluminal options are now available for closure of these perforations. Nonetheless, beyond a subjective visual inspection, the endoscopist does not have the ability to objectively test the repair for security of closure.

Physicians, and more particularly the endoscopists, in this situation are faced with two options: the endoscopist may elect to "trust" the repair and observe the patient clinically, or he or she may perform a diagnostic laparoscopy. Neither of these options is ideal. In particular, if the repair was, in fact, adequate, the patient will have been subjected to an unnecessary laparoscopy. Indeed, although laparoscopic leak tests are reliable, they represent an invasive surgical procedure and may negate some of the benefits of a purely endoscopic intervention.

However, on the other hand, significant morbidity may result if a patient is initially observed, only to later present with a leak. This issue continues to hinder the complete reliance on endoscopic closure techniques and the continued adoption of endoluminal therapies is partially hampered by the difficulty in confirming adequate luminal closure.

In view of this situation, some "leak testing" procedures have been proposed in the past, which involve a combination of endoluminal action (e.g. instilling water, colored fluids, or air under pressure) and external observation, whether by direct contact with the organ (US 2005/240093, US 2014/018696, WO 2014/074105), by outside localised detection of gases (US 2014/200437, US 2013/289367) or by sensing the change in physical parameters, such as inside pressure (US2007123781).

Nevertheless, these known leak test methods either require additional invasive surgical procedures, are not sufficiently reliable or accurate and/or need costly and time consuming imaging resources.

Given that leak tests have been recognised as an extremely valuable tool, efforts have been made to develop fully endoluminal versions. A technique that makes use of dilute hydrogen gas ($H_2$) in a leak test has been proposed. However, this test may be difficult to implement due to the need for dilute $H_2$, a gas that is not in common clinical use, is highly flamable and is not immediately available in most medical facilities. Moreover, this technique relies on specialized $H_2$ detectors, which also are not in common clinical use.

SUMMARY OF THE INVENTION

It is an aim of the present invention to overcome the limitations of the existing solutions.

For that purpose and according to one of its aspects, the invention proposes a method for detecting leaks and/or verifying adequate closure following a procedure on a hollow or tubular organ of a subject, wherein a leak test is performed by injecting or insufflating, in the concerned organ, a specific test gas which is not commonly produced or naturally present within the body of the subject, or which is present or produced in a precisely known amount or concentration, and by analysing percutaneously the gas or gas mixture present locally within the body cavity in which said organ is situated, and then verifying the presence, and preferably determining the concentration, of the injected or insufflated test gas in said resident local gas or gas mixture and indicating whether the concerned organ or a lumen defined by the latter is leak-free or not.

In an embodiment of the invention, the leak detection method comprises the step of providing a percutaneous access for detection and possibly quantification of said injected or insufflated test gas, said detection and potential quantification being performed either by sensing or by sampling locally, preferably proximately outside the lumen or organ, the resident gas or gas mixture and, if applicable, transferring the gaseous sample to a gas analysing means.

Advantageously, the percutaneous access is provided by means of an atraumatic access needle, such as a Veress needle, or a trocar, adapted and designed for establishing a fluidic communication line or a passageway between the peritoneal or thoracic cavity of the subject and a gas analysing or sensing means, said access means having possibly been put in place during an earlier procedure.

The access needle or trocar may be connected to the remote analysing means via a Luer lock tubing and may have already been placed intraoperatively in an earlier phase for insufflating in, sucking from or managing gases in the body cavity such as $CO_2$ pneumoperitoneum. If not, such a Veress needle or any analogous needle may be put in place with low morbidity and minimal post procedural discomfort.

The detection and possible quantification of the test gas can be performed by transferring at least one sample of the cavity gas mixture to a remotely located detection module or by positioning percutaneously an adapted sensor head at the tip of the access needle or trocar, through the latter, and analysing directly the gas mixture inside the cavity.

In a preferred embodiment of the invention, the test gas is a gas used during anesthesia procedures and having a short elimination half-life, and wherein the used gas analysing means may be part of an anesthesia system.

Most preferably, the injected or insufflated test gas is nitrous oxide (N2O).

Indeed, N2O has several favorable properties making it a good candidate for this application: a 0.46 blood:gas partition coefficient, a minimum alveolar concentration of 104%, and an elimination half-life of 5 minutes. The practical implication of this rapid elimination is that even if used by the anesthesiologist during the procedure, N2O may be rapidly eliminated through the respiratory system and still be utilized subsequently for a leak test according to the invention.

Furthermore, N2O is a safe, low cost inhalational anesthetic that is widely available in the clinical setting. It is distributed in compressed gas tanks which, similar to $CO_2$ tanks, may be easily connected to an endoscopic insufflator. Additionally, virtually every anesthesia machine is equipped with a nitrous oxide detector, which may be easily connected directly to a Veress needle via a simple Luer lock tubing. In various embodiments, the leak test may be performed even when unexpected perforations occur, which is arguably the time in which it is most needed.

Nitrous oxide is a non-flammable, non-irritating gas with diffusion and solubility quotients very similar to $CO_2$. At room temperature, it is relatively chemically inert. N2O has a long history of safe use in anesthesia as a weak inhaled agent, often used in combination with other inhaled anesthetics. However, prior to the present disclosure, N2O has not been used for endoscopic insufflation of a lumen, or for detecting luminal leaks following endoscopic procedures.

Nevertheless, other gases could be good candidates for test gas able to be used in the leak detection method according to the invention such as nitrogen, carbon dioxide or argon.

If there is an insufficient volume of gas inside the cavity to perform good sampling, the method according to the invention may consider having said cavity first inflated with $CO_2$ through a percutaneous access needle, before the test gas is injected or insufflated into the lumen to be checked for gas leaks, the gas or gas mixture within the cavity being then repeatedly sampled and analysed over time.

Advantageously, the concentration variation of test gas can be monitored over time, in particular its time related variation rate, as a parameter indicative of the presence of a leak.

Of course, the same access needle may have been used first for insufflating $CO_2$ into the cavity and then as access or transfer line for the gas analysis.

According to a preferred embodiment, the sampling and analysing step is performed simultaneously with, and/or immediately after, injection or insufflation of the test gas into the concerned lumen, in a synchronised manner.

In relation to an embodiment, the injection of the test gas within the concerned lumen is realised by means of an endoscopic system, preferably of the flexible type. The possible earlier diagnostic, therapeutic or surgical procedure may have taken place in the form of a mini-invasive endoscopic procedure.

Preferably the likelihood of a leak is computed, depending on the case settings, by comparing the measurement data delivered by the analysing means with stored data, for example resulting from previous measurements or inputted by an operator.

Advantageously, the test gas is injected or insufflated into the lumen to be checked, or into a tightly isolated section of the lumen, through a natural channel or orifice, which is sealed during and after the injection or insufflation phase.

Of course, the leak test described hereinbefore may be repeated as needed to re-test the integrity and tightness of the organ or lumen, or possibly the closure after a medical procedure.

According to an other of its aspects, the invention also proposes a system for detecting leaks and/or verifying adequate closure following a medical procedure, on a hollow or tubular organ of a subject, wherein said system is able to perform a leak test and comprises at least an injection module for injecting or insufflating, in the concerned organ, a specific test gas which is not commonly or naturally present or produced within the body of the subject, or present or produced in a precisely known amount or concentration, and a detection module for analysing percutaneously the gas or gas mixture locally present within the body cavity in which said organ is situated and for verifying, in cooperation with a computational module, the presence, and preferably determining the concentration, of the injected or insufflated test gas in said resident local gas or gas mixture and indicating whether or not the concerned organ or a lumen defined by the latter is leak free.

This leak detection system is thus adapted and designed to carry out the aforementioned method.

In relation to a preferred embodiment, the system also comprises a user interface for interaction of the user with the system, said interface comprising means for the user to enter information and means to display information to the user, and communicating at least with the computational module.

According to other embodiments, the injection module is adapted to control the injection of the test gas and comprises means to measure or standardise the volume, the concentration and/or the rate of injection of the test gas delivered from a corresponding source, as well as a pressure measurement means to determine the pressure within the injection tubing and/or inside the injected lumen. The detection module may comprise means providing a percutaneous fluidic access, proximate and outside the concerned lumen, to the internal volume of the cavity, wherein the organ with the lumen is located, means for transferring (a) sample(s) of the local gas or gas mixture to outside analysing means able to make a real time presence or concentration measurement of the test gas within the sample(s). The computational module may comprise means to store and to treat data provided by the other modules and by the user interface, means to communicate with and to operatively manage the injection and detection modules, means to retrieve information from the user interface and from a remote data storage and means to send information to a user interface.

In relation to a first constructive embodiment, the injection, detection and computational modules are part of an existing medical system, such as an anesthesia apparatus.

According to a second constructive embodiment, the injection, detection and computational modules, as well as the user interface are all integrated in a same independent housing, said housing also incorporating means to cooperate with a medical setting.

In relation to a third constructive embodiment, the injection, detection and computational modules, as well as the user interface are physically located in at least two separate housings, each housing or each module incorporating means for mutual wireless communication or for mutual communication through a physical link.

Advantageously, the injection module may be incorporated within a separate independent housing and constitutes, is part of or is connected to a handheld instrument, such as a flexible endoscope.

In this case, the test gas may be delivered to an endoscopic insufflator via a flow regulator.

In yet a further embodiment, the injection module and the detection module are located in housings separate from the housing incorporating the computational means, each housing comprising wireless communication means and said injection and detection modules comprising specific user interface means, for control and display.

The user interface, or main user interface, is, if not in the form of a separate unit, normally incorporated within the housing of the computational module.

Nevertheless, it may also consist in a separate device, more precisely a personal portable item belonging to the user or operator, for example a smartphone with a corresponding software application able to communicate at least with the computational module.

BRIEF DESCRIPTION OF THE DRAWINGS

Embodiments of the present disclosure will be readily understood by the following detailed description in conjunction with the accompanying drawings. To facilitate this description, like reference numerals designate like structural elements. Embodiments are illustrated by way of example and not by way of limitation in the figures of the accompanying drawings, wherein.

DETAILED DESCRIPTION OF THE INVENTION

In the following detailed description, reference is made to the accompanying drawings which form a part hereof wherein like numerals designate like parts throughout, and in which is shown by way of illustration embodiments in which the disclosure may be practiced. It is to be understood that other embodiments may be utilized and structural or logical changes may be made without departing from the scope of the present disclosure. Therefore, the following detailed description is not to be taken in a limiting sense, and the scope of embodiments in accordance with the present disclosure is defined by the appended claims and their equivalents.

Various operations may be described as multiple discrete operations in turn, in a manner that may be helpful in understanding embodiments of the present disclosure; however, the order of description should not be construed to imply that these operations are order dependent.

The description may use the phrases "in an embodiment," or "in embodiments," which may each refer to one or more of the same or different embodiments. Furthermore, the terms "comprising," "including," "having," and the like, as used with respect to embodiments of the present invention, are synonymous.

In its most preferred embodiment and application, the present invention is directed towards a method and a system 1 for detecting luminal leaks and/or verifying adequate luminal closure following an endoluminal procedure, within a hollow or tubular organ 2 of a subject 2'.

In other words, the invention encompasses a leak detection method and system for hollow or tubular organs.

The main steps and features of the inventive method have already been introduced hereinbefore and will be understood and explained in more details in relation with the system as described hereinafter, by way of examplary embodiments.

The inventive system 1 is able and designed to perform a leak test according to the method described before.

Figure 1:
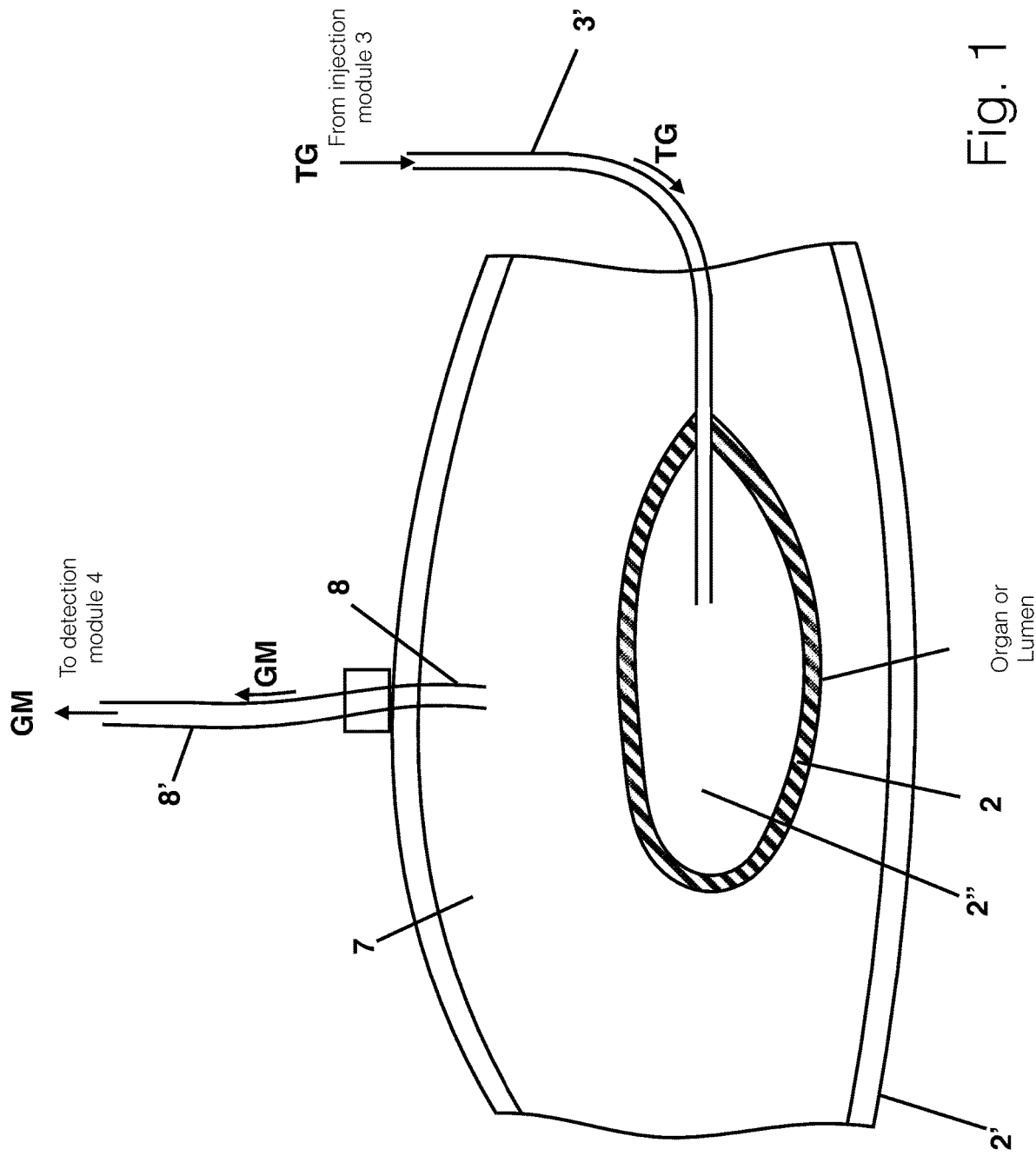
FIG. 1 is a schematic representation illustrating a site where the inventive leak testing method is applied.
Figure 2:
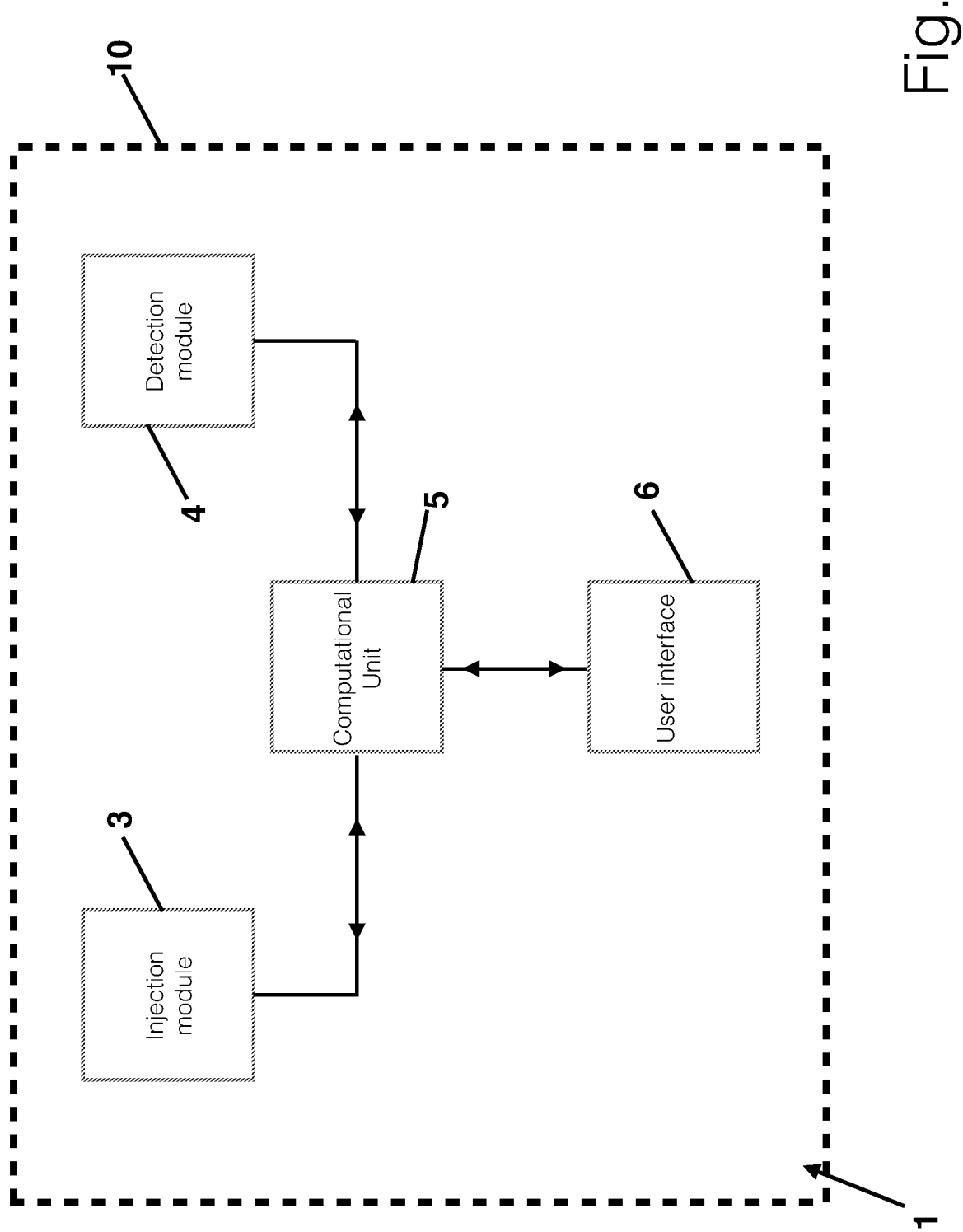
FIG. 2 is a general synoptic or block diagram of the main components of the system according to a preferred embodiment of the invention.
Figure 3:
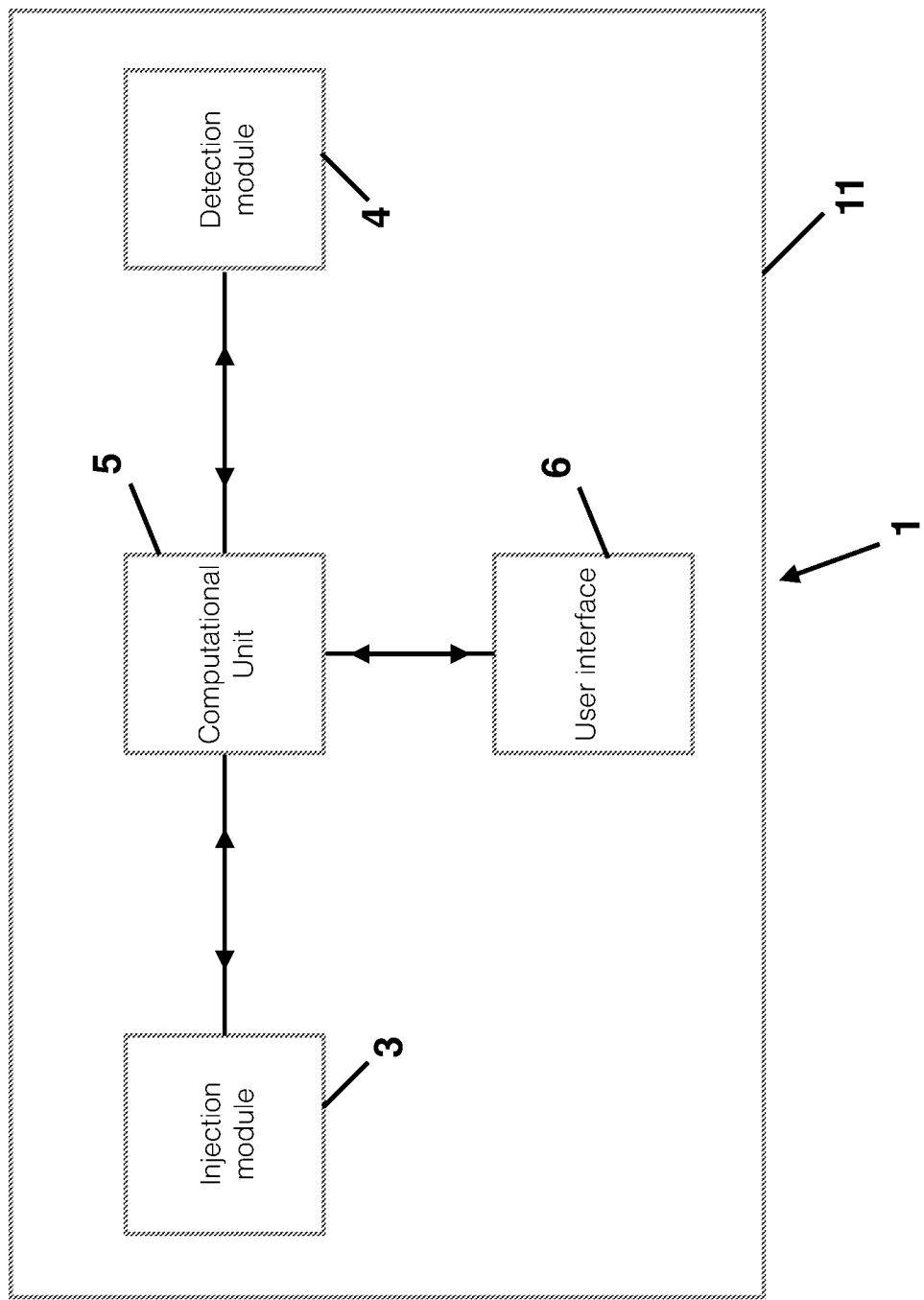
FIG. 3 is a synoptic view of a first physical construction of the system of FIG. 2, showing a single housing for all components of the system.
Figure 5:
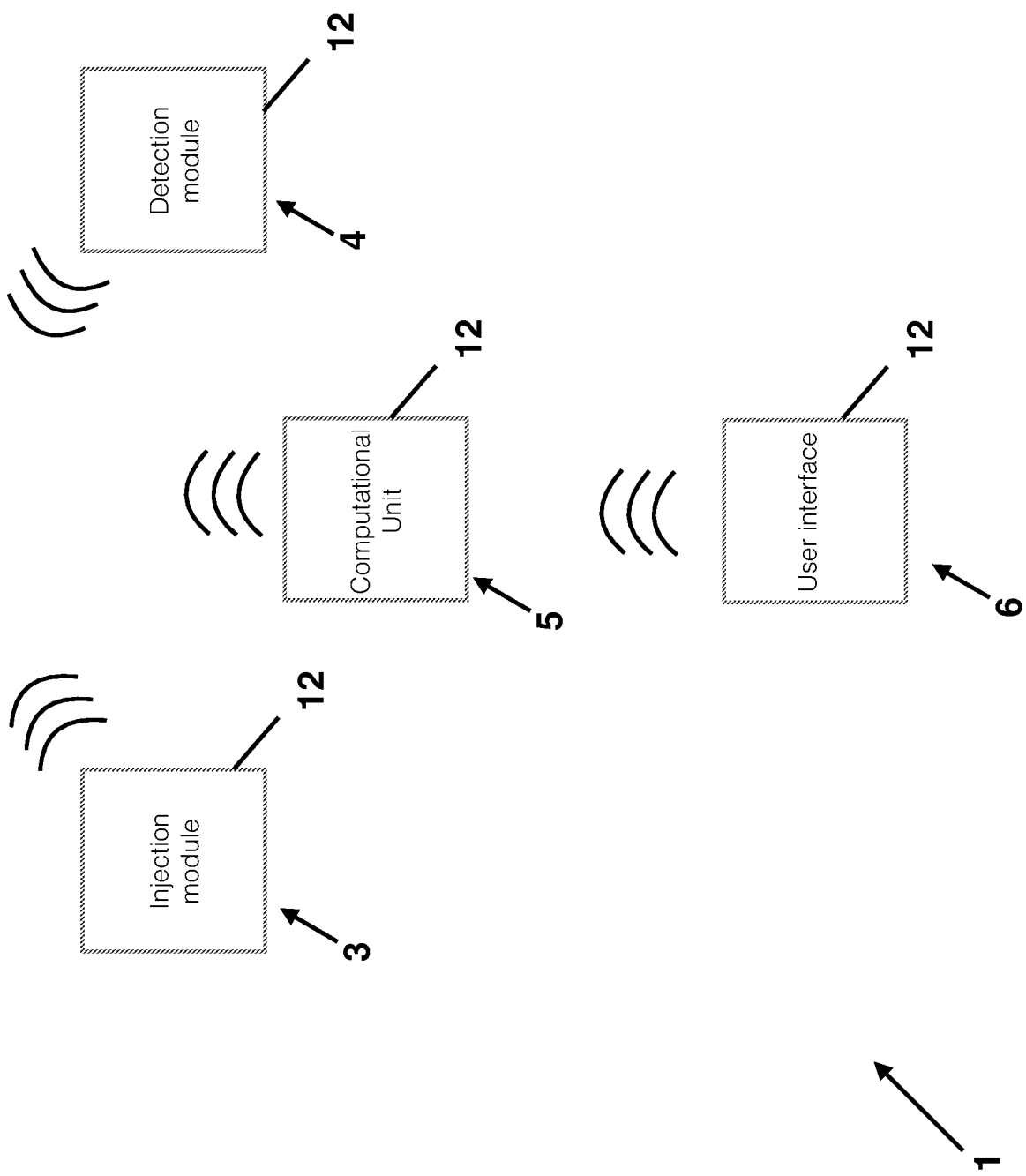
FIG. 5 is a synoptic view of a second physical construction of the system of FIG. 2, showing separate housings for the components of the system.

As shown on FIGS. 2, 3 and 5, said system 1 comprises at least an injection module 4 for injecting or insufflating, in the concerned lumen 2", a specific test gas TG which is not commonly or naturally present or produced within the body of the subject 2', or present or produced in a precisely known amount or concentration, a detection module 3 for analysing percutaneously the gas or gas mixture GM locally present within the body cavity 7 in which said organ 2' comprising said lumen 2" is situated and for verifying, in cooperation with a computational module 5, the presence, and preferably determining the concentration, of the injected or insufflated test gas TG in said resident local gas or gas mixture GM and indicating whether or not the concerned lumen 2" is leak free.

As also shown on said figures, the system 1 also comprises a user interface 6 for interaction of the user with the system 1, said interface comprising means for the user to enter information and means to display information to the user, and communicating at least with the computational module 5.

As can be seen from the attached schematic drawings and as exposed hereinbefore and after, the invention concerns, on the one hand, an endoluminal leak detection method and, on the other hand, an endoluminal leak detection system, representing two aspects of the same invention.

Although the following specification is more generally directed towards the system 1, the major features inventive method can be easily derived from the various functions performed by the different components 3, 4, 5, 6 of the system 1.

Fundamentally, the system 1 is adapted and designed to control the injection of a test gas TG into a hollow organ 2 to be checked for leaks and to measure if the test gas is leaking in an adjacent space (internal free volume of the body cavity 7 containing the organ 2). The leak detection system 1 computes the likelihood of a leak and this information is then displayed to the user. A computational module 5 is provided to synchronize and control the parameters of the injection process and of the detection process, manage the various components of the system, interpret user input and compute the likelihood of a medically relevant leak in the aforementioned hollow organ 2 and display that information to the user. The computation is based on stored data (possibly retrieved from a remote storage 9), information entered by the user and the gas measurement information.

Thus, the leak detection system 1 computes the likelihood of a medically relevant leak in the aforementioned hollow organ 2. It generally comprises an injection module 3, a detection module 4, a computational module 5 and a possible user interface 6.

According to various embodiments of the present invention, said leak detection system 1 is adapted to be used in different clinical settings such as, but not limited to, flexible endoscopy procedures, laparascopic procedures, open surgery procedures, percutaneous procedures or radiologic procedures. Depending on the clinical setting the cooperation and communication between the constitutive means and components of the leak test system 1 may vary.

By comparing the system configurations and constructions illustrated in FIGS. 2, 3 and 5, the person skilled in the art will understand that the preferred four functional units 3, 4, 5, 6 of the system 1 may be either incorporated, partly or completely, in a more global medical system 10 for example an anesthesia apparatus (rectangle of broken lines of FIG. 2); all accommodated together in a single housing 11 (see FIG. 3) or each incorporated separately in its own independent housing 12 (see FIG. 5).

The three main constitutive modules 3, 4 and 5 will now be described in more details, according to various possible embodiments and in relation to different constructive alternatives of the system 1.

Figure 4:
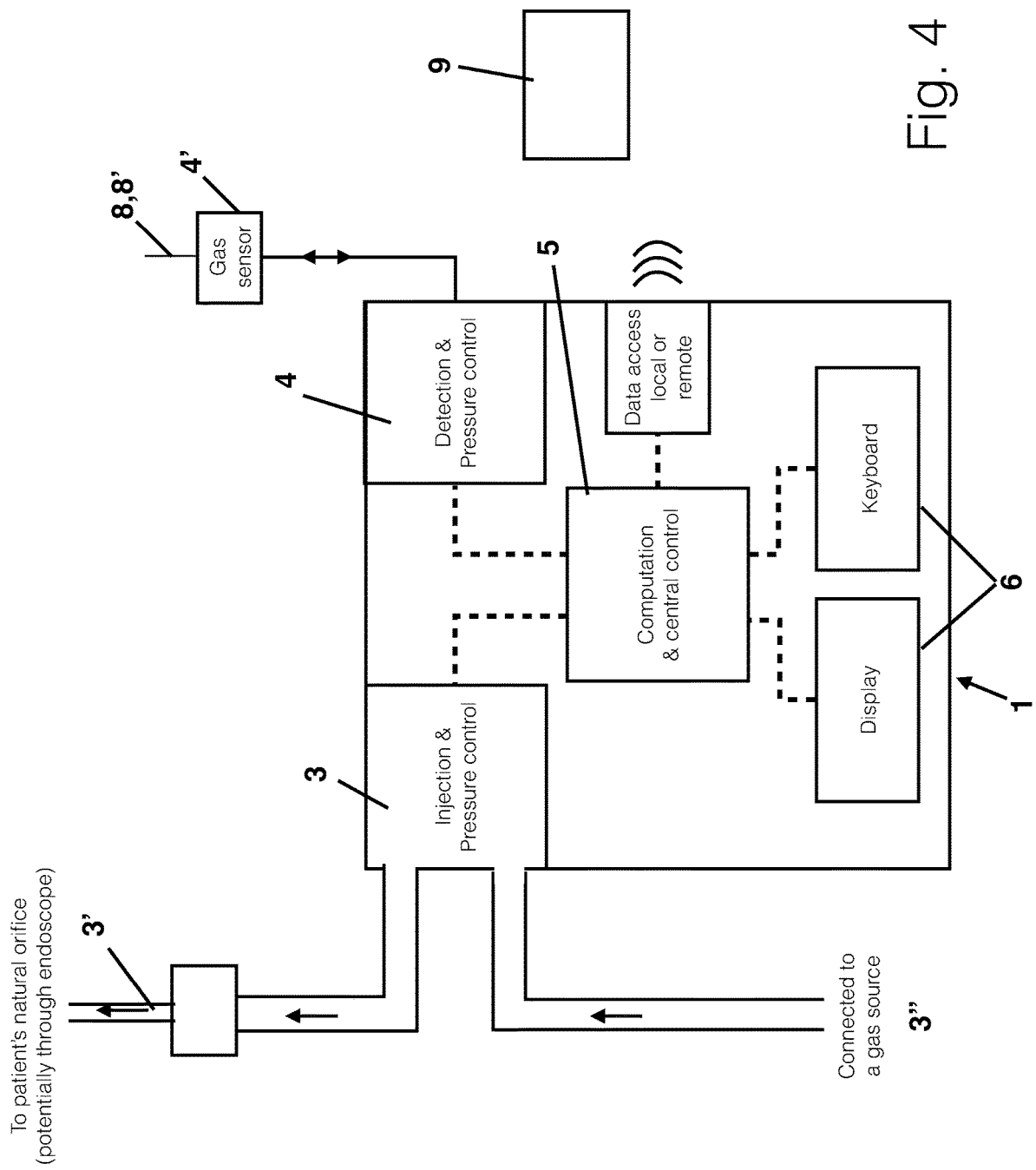
FIG. 4 is a functional block diagram of the constructive embodiment of the system of FIG. 3.
Figure 8:
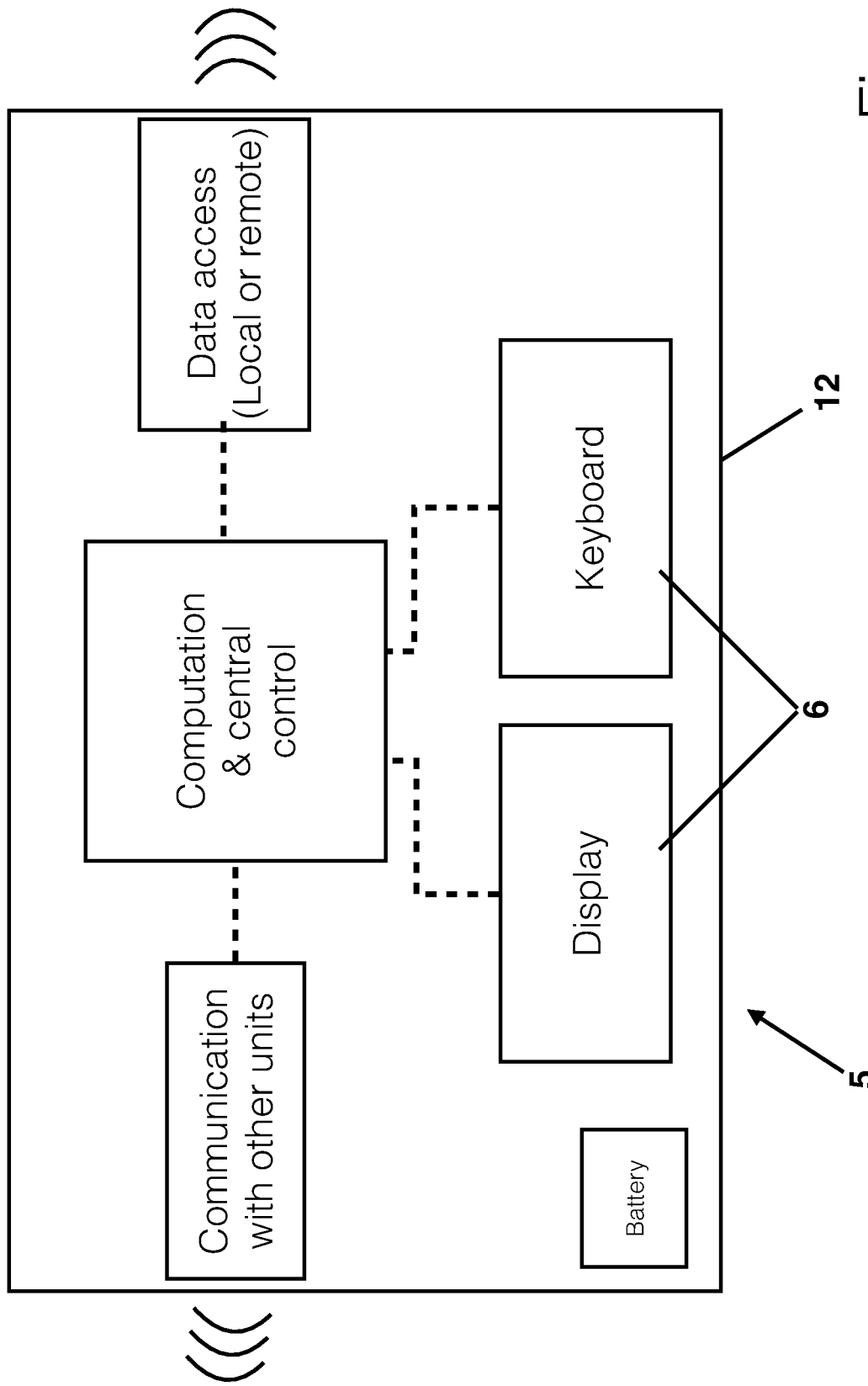

Computational Module (FIGS. 4, 8 and 9)

The computational module 5 acts as the central unit of the system 1. Based on stored data and information entered by the user, it computes parameters of the leak test to be performed and controls the detection module 3 and the injection module 4 to perform the leak test. During the leak test, the computational module 5 receives and interprets continuously information sent by the detection module 4 and the injection module 3.

Said computational module 5 has computational power, communication capabilities with the injection module 3, the detection module 4 and a possible user interface 6. Said computational module also comprises remote and/or local data storage 9.

The computational module 5 may send instructions to the injection module 3 and the detection module 4 and can receive information from them. The computational module 5 can send information to the user interface 6 to be displayed to the user and can interpret information coming from the user interface 6. The computational unit 5 can access and interpret data from both local and remote storages (local storage means may be integrated with the communication and computation means in hybrid circuits or as separate circuits on electronic PCB).

The computational module is adapted to interpret information entered by the user, which may include parameters describing the clinical setting and potentially influencing the measurement such as for example: weight, age, sex of the patient, site of potential perforation, indication about the estimated size of the perforation.

When the modules are mounted in separate housings 12, the computational module 5 ensures the communication with the detection module 4 and the injection module 3. It also displays the information that the system 1 is ready to perform a leak test to the user on the particular user interfaces 13' integrated in the computational module 5, in the detection module 4 and in the injection module 3. The user then places and connects the cooperation means integrated in the detection module 4 and in the injection module 3, depending on the clinical setting and on the organ to be checked.

By using another of the specific user interfaces 13' (input), the user can then start the leak test.

Figure 6:
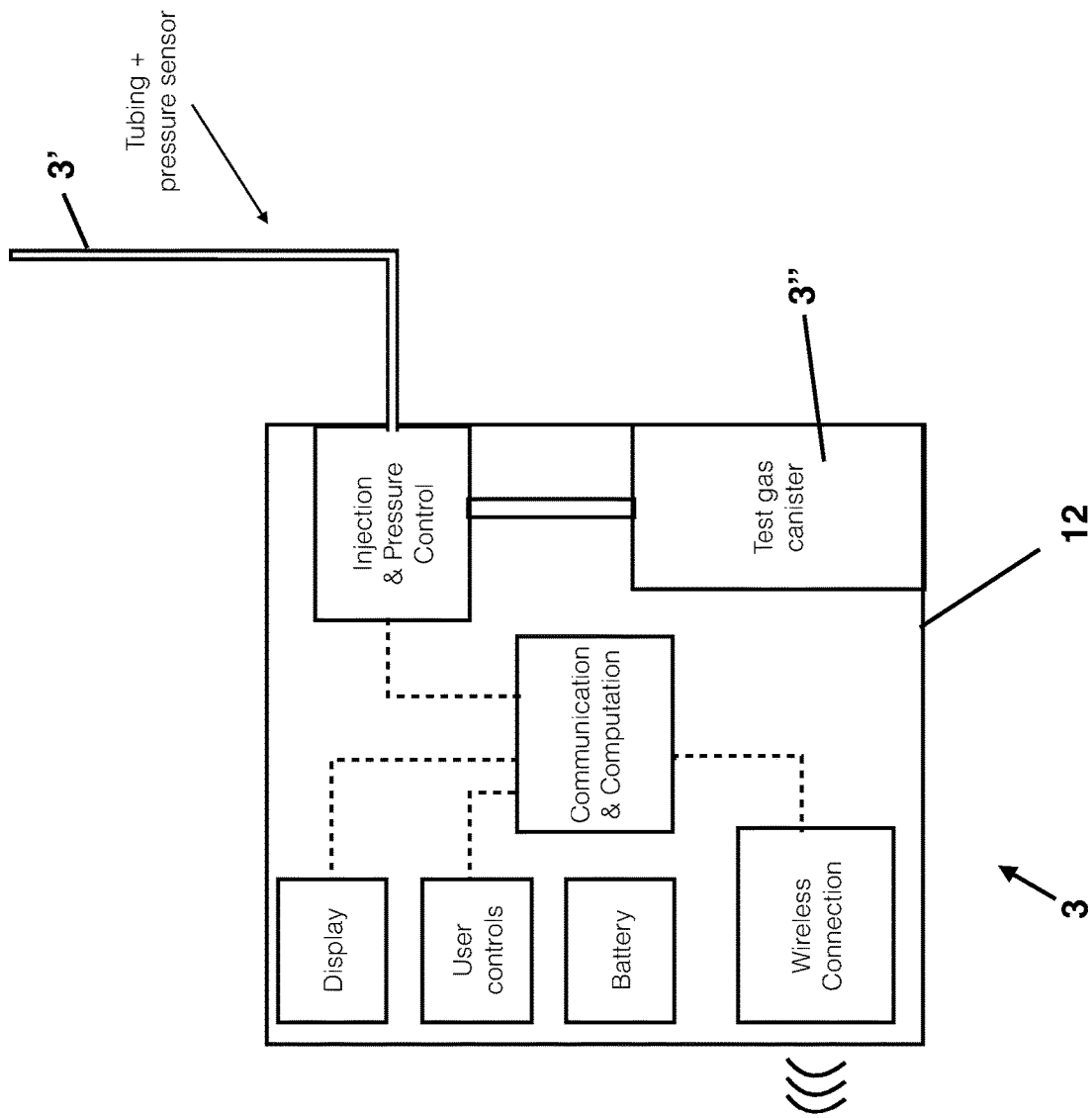
FIG. 6 is a functional block diagram of the injection module which is part of the system shown on FIG. 5.

Injection Module (FIGS. 4 and 6)

The injection module 3 is intended to inject a test gas TG inside a hollow organ 12 to be tested and to control and measure parameters of this injection such as the volume of gas injected, the concentration and/or the rate of injection, and also the pressure at the injection site.

In a general embodiment, the injection module comprises a connection to a pressurised source 3" of test gas TG, a gas carrying element, means to control the inlet of test gas in the gas carrying element 3' and means to communicate with the computational unit 5 and to interpret information received.

In one embodiment, the pressurised source 3" of test gas is a disposable container and the injection module comprises a connection system configured to adapt to the container. In another embodiment, the pressurised source of test gas may be a gas delivery line of a corresponding distribution network.

In one embodiment, the injection module 3 comprises a communication means to exchange information or instructions with the detection module 4 and/or the computational module 5 and means (computational resources) to interpret any information or instructions received. Information and instructions transferred include but are not limited to, beginning and end of the gas injection, volume of gas injected, type of gas injected, pressure at the injection site (see FIG. 6).

According to the present invention, the injection module 3 comprises a test gas TG carrying element 3' to carry the test gas to the test site. The test gas can be carried to the desired site by different entries/approaches depending on the clinical setting.

In one embodiment, the gas carrying element is a tube 3' adapted for insertion in the human body 2'. Such a gas carrying element can be manufactured in a bio-compatible material, for example a plastic or metal. For example, in the case of colorectal surgical procedures, the gas carrying element is adapted for anal insertion and may include means to seal the anal orifice.

In another embodiment, the gas carrying element is adapted to be inserted inside the working channel of a diagnostic or surgical apparatus such as a flexible endoscope (not shown).

In another general embodiment, the injection module 3 and the computational module 5 may not be integrated in the same housing. In such an embodiment, said communication means of said injection module 3 may for example be radio-frequency or wire based (FIG. 6).

In one embodiment, the injection module 3 may comprise an independent power supply such as batteries or means to connect it to a standard power outlet (FIG. 6).

In one embodiment, the injection module 3 comprises a specific user interface comprising means 13 to display information to the user such as, but not limited to, confirmation of the data connection between said injection module 3 and said computational module 5, beginning and ending of the injection of said test gas, the amount of gas remaining in the container 3", an indication of the pressure level inside the gas container 3", an indication of the general status of the injection module 3, an indication of the pressure at the injection site.

Said injection module 3 may also comprise a specific user interface 13' with user controls, enabling a user to control the injection of said test gas and comprising for example controls such as: stopping, starting or controlling parameters of said injection of said test gas or turning the injection module on or off or settings designed for differing organ systems.

In one embodiment, the injection module 3 is integrated in an independent housing 12 and may be adapted to be used as a handheld instrument. In this embodiment, the housing may for example be adapted to be connected to a disposable canister 3" filled with the test gas.

In another embodiment, the injection module 3 may be adapted to be used during a flexible endoscopy procedure. The injection module 3 may thus be substantially compact and may include a means to anchor the injection module to the handle of a flexible endoscope. The injection module may also be reversibly connected to the gas carrying element 3'.

Figure 7:
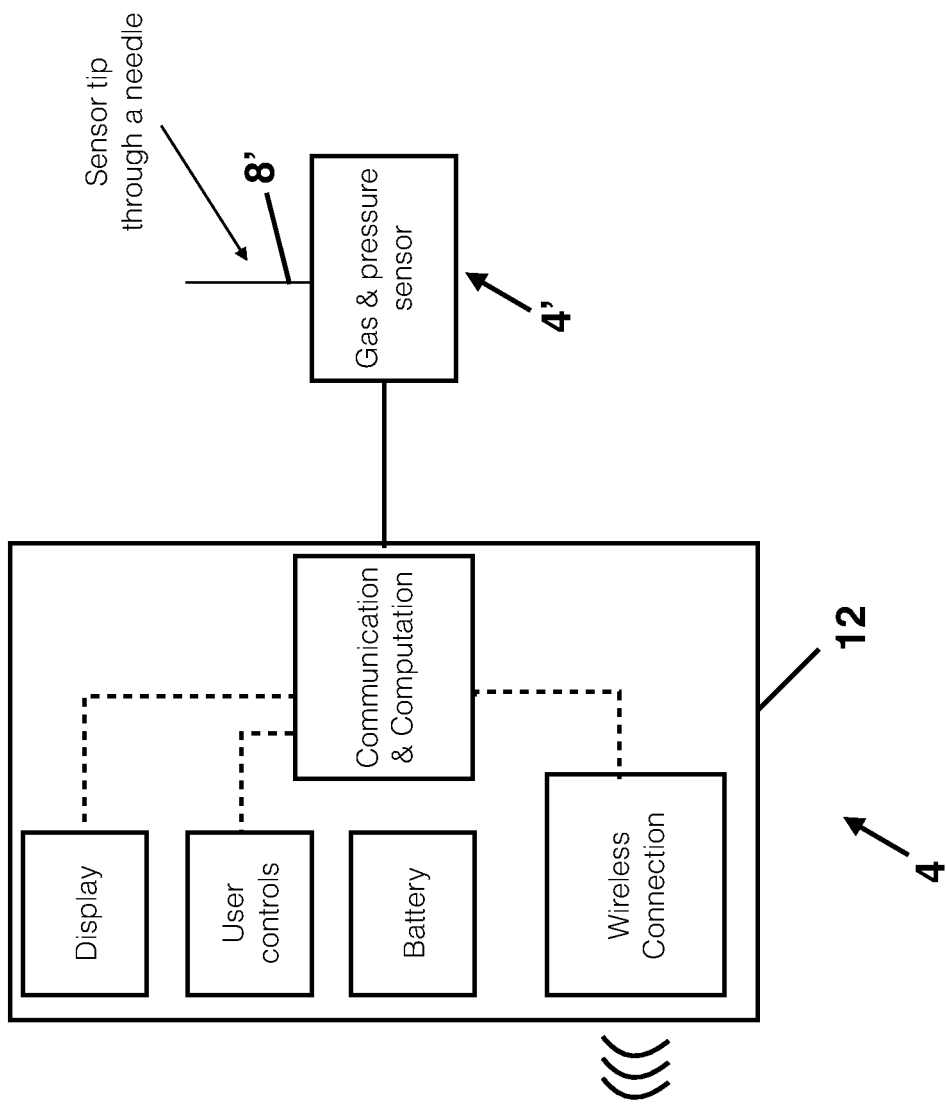
FIG. 7 is a functional block diagram of the detection module which is part of the system shown on FIG. 5, and, FIGS. 8 and 9 are alternative functional block diagrams of the computational module which is part of the system shown on FIG. 5, according to two different embodiments of the user interface.

Detection Module (FIGS. 4 and 7)

The purpose of the detection module 4 is to make a real time measurement in order to determine the presence and/or concentration of a test gas in a region adjacent an organ 2 to be checked. The detection module 4 is adapted to measure parameters such as (but not limited to) the concentration of at least one specific gas, or the pressure at the measurement site.

In an embodiment, the detection module comprises a sensor 4' adapted to detect the test gas TG, an access device 8 granting access to the zone adjacent to the hollow organ 2, means to communicate with the computational module 5 and means to interpret information received from the computational module (computational resources).

In one embodiment, the detection module 4 comprises means to communicate information to the injection module 3 and/or the computational module 5 and means to interpret any information or instructions received. Transferred information and instructions include but are not limited to, beginning and end of the gas measurement, concentration of gas measured, pressure at the measurement site.

According to the present invention, the detection module 4 also comprises an access element 8 to either introduce the measuring element (tip of the sensor 4') within the body cavity 7 containing the organ 2 and preferably adjacent said organ 2 to be checked or, in cooperation with transfer tubing 8', to carry the gas or gas mixture (GM) potentially present from a zone adjacent the organ 2 to be checked to the measuring element and analysing means of the detection module 5 located outside the body. The access element 8 can vary depending on the clinical setting.

In a general embodiment, the access element 8 comprises a needle to be inserted through a biological tissue to reach a zone adjacent to the organ 2 to be checked.

In one embodiment, the measurement means 4' is placed within the passageway of the hollow shaft of the needle 8 and introduced in said cavity 7 through said passageway.

In another embodiment, gas is carried through the shaft of the needle 8 to the measurement means 4', for example by using a hollow connector and tubing 8'.

In another general embodiment, in the case of laparoscopic surgery, the access element 8, for example a hollow tube, may be connected to a trocar. This configuration allows the system to be used quickly.

In one embodiment, the detection module 4 may comprise an independent power supply such as batteries or means to connect it to a standard power outlet.

In another embodiment, the detection module 4 comprises a specific user interface comprising means 13 to display information to the user such as, but not limited to, confirmation of the data connection between said detection module 4 and said computational module 5, beginning and ending of the detection of said test gas, a real time indication of the concentration of test gas or fluid measured, an indication of the general status of the detection module, an indication of the result of the computation, that is whether the system has determined that a leak was present or not.

Said user interface of said detection module 4 may also comprise user controls 13' enabling a user to control the detection of said test gas comprising for example controls such as stopping or starting said detection of said test gas.

In one embodiment, the detection module is integrated in an independent housing and may be adapted to be used as a handheld instrument.

The disclosed minimally-invasive method and system for assessing the integrity of an organ or lumen may provide numerous advantages. For instance, they may enable the objective detection of an ongoing gas leak, confirming that further endoscopic or operative management is required. Additionally, they may provide objective evidence of adequate repair, which may avoid performance of a negative diagnostic laparoscopy or prevent invasive procedures such as a colostomy to be performed. Moreover, they may prevent invasive procedures in a large portion of patients, as the Veress other needle or a trocar may have already been placed intraoperatively Although certain embodiments have been illustrated and described herein for purposes of description of the preferred embodiment, it will be appreciated by those of ordinary skill in the art that a wide variety of alternate and/or equivalent embodiments or implementations calculated to achieve the same purposes may be substituted for the embodiments illustrated and described without departing from the scope of the present invention. Those with skill in the art will readily appreciate that embodiments in accordance with the present invention may be implemented in a very wide variety of ways. This application is intended to cover any adaptations or variations of the embodiments discussed herein. Therefore, it is manifestly intended that embodiments in accordance with the present invention be limited only by the claims and the equivalents thereof.

The invention claimed is:

1. A method for computing the likelihood of a medically relevant leak in a hollow organ of a patient, said hollow organ being located inside a body cavity of the patient, said method being implemented by means of a system comprising:

an injection module comprising a pressure measurement component and being configured for injecting a test gas from a gas container to said hollow organ, said test gas being a gas that is not naturally present within said body cavity, or said test gas being naturally present within the body cavity in a known amount or concentration, said injection module being configured to control injection or insufflation of the test gas and measure or standardize at least one of a volume, concentration, detected test gas pressure in the hollow organ, or rate of injection of the test gas delivered from said gas container; and said pressure measurement component being configured to determine a pressure within at least one of an injection tubing of said injection module or inside said hollow organ, a detection module comprising a gas analyzing component that makes a real time presence or concentration measurement of the test gas within a gaseous sample and a transferring component configured to transfer the gaseous sample of at least one gas or gas mixture from the internal free volume inside the body cavity to the gas analyzing component, and a computational module with a user interface and a remote and/or local data storage for computing the likelihood of a medically relevant leak based on stored data, information entered by the user, and gas measurement information, the computational module communicating with both the injection module and the detection module;

the injection module, the detection module, and the computational module being all located outside the patient, said method comprising the steps of:

the user entering into the remote and/or local data storage of the computation module via the user interface parameters related to the patient, and parameters describing the site of the potential leak within the hollow organ;

accessing, by the computation module, data resulting from previous measurements, the parameters related to the patient, and the parameters entered by the user describing the site of the potential leak within the hollow organ;

interpreting, by the computational module, the data resulting from previous measurements, the parameters entered by the user related to the patient, and the parameters entered by the user describing the site of the potential leak within the hollow organ;

computing, by the computational module, injection parameters comprising one or more of: volume of gas injected, concentration of the gas injected, rate of injection, and pressure at the injection site, the computing based on the data resulting from previous measurements, the parameters entered by the user related to the patient, and the parameters entered by the user describing the site of the potential leak within the hollow organ;

completing a computer controlled injection according to the injection parameters, the computer controlled injection comprising the steps of:

i. accessing the inside of the hollow organ and also accessing the body cavity;

ii. injecting, in a controlled manner, the test gas into the organ;

quantifying, simultaneously with said injecting and in real time, by means of the detection module a concentration of said test gas in said body cavity, the concentration of the test gas comprising measurement data; —transferring, by means of the transferring component of the detection module, at least one sample of a gas mixture from within said body cavity to the gas analyzing component:

analyzing, by means of the gas analyzing component of the detection module, said at least one sample of a gas mixture transferred from within said body cavity to make a real time presence or concentration measurement of the test gas within the transferred at one least sample;

computing the likelihood of a medically relevant leak by comparing the measurement data delivered by the detection module with the data resulting from previous measurements, the parameters entered by the user related to the patient, and the parameters entered by the user describing the site of the potential leak within the hollow organ; and displaying the likelihood of a medically relevant leak in the hollow organ of the patient to a user, wherein said injecting and said determining are performed in a synchronized manner under the operative management and control of the computation module, the computational module continuously receiving and interpreting information sent by the injection module and the detection modules, and sending instructions to both said injection and detection modules to operatively manage and control the injection and detection modules and injection and determining steps, including parameters of the injecting and determining steps.

2. The method according to claim 1, wherein said accessing the body cavity in which the hollow organ is located is performed percutaneously.

3. The method according to claim 2, wherein said percutaneous accessing is provided by an atraumatic access needle configured to establish a fluidic communication line or a passageway between the body cavity and a detection module.

4. The method according to claim 1, wherein the test gas is a gas used during anaesthesia procedures.

5. The method according to claim 1, wherein the test gas is nitrous oxide ($N_2O$).

6. The method according to claim 1, further comprising: before said injecting, inflating the body cavity with CO2 through a percutaneous access needle; repeatedly sampling and analyzing the gas mixture within the body cavity; and monitoring the concentration of, and a variation rate of the concentration of, the test gas in the body cavity over time.

7. The method according to claim 1, further comprising: prior to said quantifying, analysing percutaneously the resident gas or gas mixture present within the body cavity.

8. The method according to claim 1, wherein said injection is accomplished by means of an endoscopic system.

9. The method according to claim 8, wherein said endoscopic system is of a flexible type endoscopic system.

10. The method according to claim 1, wherein said injecting takes place through a natural channel or orifice, the natural channel or orifice being sealed during and after said injecting.

11. The method according to claim 1, wherein said injecting is into a section of the hollow organ that is sealed during and after the injection phase.

12. The method according to claim 1, wherein the hollow organ is a lumen.

13. The method according to claim 1, further comprising, prior to said quantifying percutaneously analyzing a gas or gas mixture present in the body cavity.

14. The method according to claim 1, wherein the injection module is controlling the injection of the test gas by measuring or standardising the volume, the concentration and/or the rate of injection of the test gas delivered from a gas container, as well as by determining the pressure within the injected hollow organ.

15. The method according to claim 1, wherein the injected test gas is not a gas that is naturally present within said body cavity.

16. The method according to claim 1 wherein the injection parameters comprise each of: volume of gas injected, concentration of the gas injected, rate of injection, and pressure at the injection site.

* * * * *